United States Patent [19]

Roth

[11] Patent Number: 4,986,986

[45] Date of Patent: Jan. 22, 1991

[54] SKIN MOISTURIZING AND OIL RESTORING LOTION

[76] Inventor: Nora Roth, S.I.P. Inc., P.O. Box 9511, Alexandria, Va. 22304

[21] Appl. No.: 351,690

[22] Filed: May 15, 1989

Related U.S. Application Data

[63] Continuation-in-part of Ser. No. 238,258, Aug. 30, 1988, abandoned.

[51] Int. Cl.$^5$ ...................... A61K 35/78; A61K 31/20
[52] U.S. Cl. .................... 424/195.1; 514/558; 514/783; 514/844; 514/845; 514/846; 514/847
[58] Field of Search ...................... 424/195.1; 514/783, 514/844, 845, 846, 847, 558

[56] References Cited

U.S. PATENT DOCUMENTS

| | | | |
|---|---|---|---|
| 624,925 | 5/1899 | Grapewine | 424/58 |
| 1,516,562 | 11/1924 | Calabro | 424/195.1 X |
| 1,631,384 | 6/1927 | Richmond | 424/195.1 |
| 3,463,862 | 8/1969 | Mazza | 514/776 |
| 4,297,374 | 10/1981 | Wess | 514/777 |
| 4,395,424 | 7/1983 | Veney | 514/846 |
| 4,525,344 | 6/1985 | Tutsky | 424/73 |

FOREIGN PATENT DOCUMENTS 2388555 12/1978 France .................. 424/195.1

*Primary Examiner*—John W. Rollins
*Attorney, Agent, or Firm*—Armstrong, Nikaido, Marmelstein, Kubovcik and Murray

[57] ABSTRACT

A skin moisturizing lotion produced by blending specific quantities of peanut oil, rose water, olive oil, anhydrous lanolin, and natural lemon oil. The ingredients are blended to a fluid texture and applied to the skin in quantities as desired by the user. The product contains no alcohol, emulsifiers or preservatives. It may be stored at temperatures ranging from about 55° to 90° F. and, preferably 59° to 86° F.

2 Claims, No Drawings

SKIN MOISTURIZING AND OIL RESTORING LOTION

This application is a continuation-in-part of prior application Ser. No. 238,258 filed Aug. 30, 1988, now abandoned.

BACKGROUND OF THE INVENTION

This invention relates to the art of cosmetics and, more particularly, to an improved moisturizing lotion, devoid of artificial ingredients, preservatives, emulsifiers and alcohol. Such agents, although contributing to the stability and preservation of the cosmetic, can actually dry the skin, or are beneficially neutral.

DISCUSSION OF RELATED ART

French Pat. Publication No. 2 388 555 (Haguenauer) discloses a "nourishing cream for protecting dry skin" which is essentially a lanolin compound, containing the lanolin as its primary and dominant ingredient (60%). The lanolin is treated by heating and mixed with minor amounts of orange juice (other fruit juices may be substituted), almond oil and rose water.

U.S. Pat. No. 4,297,374 (Wess) discloses a moisturizing and cleansing cream blend of fresh bananas or avocados, baking powder, orange juice and solid or liquid vegetable shortening.

U.S. Pat. No. 3,810,006 (Sutliff) provides two separate mixtures which are separately applied to the skin and are otherwise never combined. The first mixture combines olive oil and almond oil which is applied to the skin as an oil base and then an aqueous paste is applied over the oil base. The paste contains from 80%-90% milk solids and approximately 20% dried banana flour.

U.S. Pat. No. 4,395,424 (Veney) employs a mixture of water, non-fat dry milk solids, witch hazel and olive oil as a cosmetic cream. The mixture can also contain emollients, preservatives and fragrances such as polyoxyethylene and methylparaben.

U.S. Pat. No. 3,463,862 (Mazza) discloses a cosmetic lotion using as its essential ingredients albumin, an astringent, and an oil. A typical composition includes proportionate amounts of linseed oil, benzoic acid, egg whites, alum, lanolin, corn oil, glycerin and liquid petrolatum.

U.S. Pat. No. 624,925 (Grapewine) discloses a skin lotion or cream consisting essentially of cooked and defibrated lemon and salt.

U.S. Pat. No. 1,516,562 (Calabro) discloses a hair fortifying and scalp conditioning composition consisting essentially of a cooked and strained mixture of lemon juice, olive oil and powdered sulfur mixed with oil of bergamot, bicarbonate of soda and alcohol.

U.S. Pat. No. 1,631,384 (Richmond) discloses a skin lotion containing pure citrus pectin (e.g., lemon pectin) to which other materials may be added including glycerine, soaps, oils, emulsified oils, lanolin, almond oil, stearic acid, alkali stearates and the like.

An object of the present invention is to provide a cosmetic composition containing no artificial ingredients, preservatives, emulsifiers or alcohol.

It is also an object of this invention to provide a cosmetic composition which does not contain fruit juices of any kind and contains only a minor amount of lanolin.

Another object of the instant invention is to provide a cosmetic composition with no artificial ingredients, which will provide a moisturizing effect when applied to the skin.

A further object of the instant invention is to restore oils to the skin which are lost through exposure to wind and sun, and to lock in the natural moisture of the skin.

A further object of the instant invention is to provide a natural skin cleansing cream.

A still further object of the invention is to provide a moisturizing lotion which is effective on all skin types, which when applied, will provide a soft and smooth texture to the skin.

SUMMARY OF THE INVENTION

According to the present invention a skin moisturizing lotion is provided which contains specific quantities of all natural ingredients including peanut oil, rose water, olive oil, anhydrous lanolin and natural lemon oil.

The lotion, when applied to the skin, leaves the skin moisturized, restores oils and gives the skin a healthy glow. The natural ingredients of the lotion of the invention are also especially effective in removing dirt and make-up. The lotion contains only natural ingredients yet has an indeterminable shelf life.

DESCRIPTION OF PREFERRED EMBODIMENTS

The skin moisturizing lotion of the invention contains, by volume, from about 40 to 55% of peanut oil, 15 to 22% of olive oil, 10 to 20% of lanolin, 20 to 30% of rose water and 0.35 to 0.65% of lemon oil. In a preferred embodiment, the lotion contains, by volume, 15% olive oil, 45.5% peanut oil, 15% lanolin, 24% rose water and 0.5% lemon oil.

The skin moisturizing and oil restoring lotion of the present invention is prepared by a specific procedure which provides high storage stability. Specifically, the peanut oil is blended in a high speed blender with the pure olive oil and pure anhydrous lanolin at a low speed until a smooth texture is achieved. Rose water and natural lemon oil are added to the mixture and blended at medium speed until completely homogeneous and fluid, e.g., approximately three minutes. Instead of a blender, an electric mixer or beater can be employed to obtain the lotion.

The lotion prepared in this manner, when stored at temperatures ranging from 55 to 90.F, preferably 59 to 86.F, has indeterminable shelf life without emulsifiers, stabilizers, preservatives or the like.

What is claimed is:

1. A skin moisturizing and oil restoring composition consisting essentially of:
   (A) 40 to 55% by volume of peanut oil,
   (B) 15 to 22% by volume of olive oil,
   (C) 10 to 20% by volume of anhydrous lanolin,
   (D) 20 to 30% by volume of rose water, and
   (E) 0.35 to 0.65% by volume of lemon oil,
   based on the volume of the composition.

2. A skin moisturizing and oil restoring composition consisting essentially of:
   (A) 45% by volume of peanut oil,
   (B) 15% by volume of olive oil,
   (C) 15% by volume of anhydrous lanolin,
   (D) 24% by volume of rose water, and
   (E) 0.5% by volume of lemon oil,
   based on the volume of the composition.

* * * * *